United States Patent [19]

Kashman et al.

[11] Patent Number: 4,857,538
[45] Date of Patent: Aug. 15, 1989

[54] NEW COMPOUNDS FOR THE STUDY AND TREATMENT OF MICROFILAMENT ORGANIZATION IN CELLS

[75] Inventors: Yoel Kashman, Tel Aviv; Ilan Spector, Port Jefferson, N.Y.; Shmuel Carmely, Neve Monoson; Dina Blasberger, Petah Tikva, both of Israel

[73] Assignee: The Research Foundation of State University of New York, Albany, N.Y.

[21] Appl. No.: 126,364

[22] Filed: Nov. 30, 1987

[51] Int. Cl.⁴ .................. C07D 493/08; A01K 31/425
[52] U.S. Cl. ..................................... 514/369; 548/187
[58] Field of Search ........................ 548/187; 514/369

[56] References Cited
PUBLICATIONS

March, Advanced Org. Chem. pp. 796–798 (1985).

Primary Examiner—Robert Gerstl
Attorney, Agent, or Firm—Hoffmann & Baron

[57] ABSTRACT

A compound, and composition including same, for effecting irreversible change in cell morphology having the following structures:

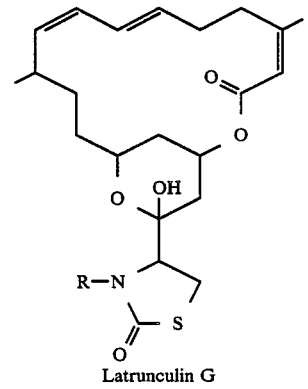

Latrunculin G

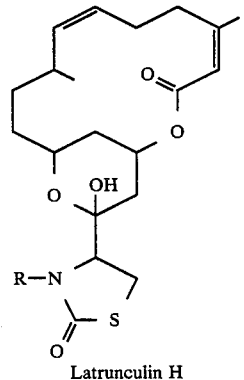

Latrunculin H wherein R is —$(CH_2)_n$ZH in which n=1, 2, 3 and 4 and Z is O, S, or NH, and

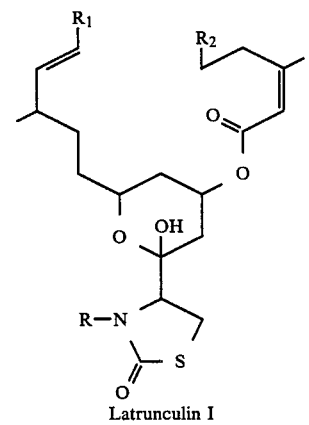
Latrunculin I wherein $R_1$ and $R_2$ can be —OH, alkyl and acyl.

4 Claims, No Drawings

NEW COMPOUNDS FOR THE STUDY AND TREATMENT OF MICROFILAMENT ORGANIZATION IN CELLS

The present invention relates to new bioeffecting compounds, and, in particular, to such compounds which have profound effect on actin structure in cells and inhibit microfilament-mediated cellular processes.

Actin, the major constituent of the 6–8 nm wide microfilaments is present in all eukaryotic cells, and in most cells it is the most abundant protein. Much is known about the structure and biochemistry of actin and it is widely accepted that actin microfilaments play a major role in a wide range of cell motility phenomena and in cell shape determination. The role of actin is best understood in striated muscle cells where all the actin is permanently polymerized and forms stable, highly ordered structures. However, in nonmuscle cells actin is found both in the polymer form (F-actin) and as a monomer (G-actin). In these cells actin microfilaments are highly dynamic structures that are being constantly formed and broken down in response to a host of stimuli. Furthermore, assembly and disassembly of actin filaments may take place concomitantly in different regions of the cell. These features make the study of the organization and function of microfilaments in nonmuscle cells difficult and present a major challenge for present day cell biology.

A fundamental approach to investigate the organization of actin microfilaments or other cytoskeletal components in nonmuscle cells and to relate this organization to the physiological state of the cell is to use specific drugs that will interfere with the state of organization of a given component in vivo and in vitro and affect cell behavior. The potential inherent in this approach has been realized in microtubule research where the extensive use of the relatively large arsenal of microtubule poisons has enhanced considerably our understanding of the organization and functions of this cytoskeletal component.

However, in the case of microfilaments this approach has been rather restricted, since, to date, only a few drugs have been found to interfere with cellular activities by reacting specifically with microfilaments. The most popular class of these compounds are the fungal metabolites cytochalasins. These low molecular weight compounds readily enter the cell and exert profound effects on cell shape, actin organization, and on many kinds of cell motility phenomena such as cell locomotion, cytokinesis, and phagocytosis. Since the discovery of their effects on cells in 1967, cytochalasins have been used extensively as tools for the identification of actin-mediated cellular processes although their mode of action at the molecular level was not known until 1979.

There is now strong evidence that the cytochalasins bind to the rapidly growing (barbed) end of F-actin and block all association and dissociation reactions at those ends. In vivo, the effects of cytochalasins on microfilament organization, cell morphology and cell function are presumed to be due to their competition with physiologic barbed-end capping agents. The other widely known drug that reacts specifically with actin is the toadstool peptide phalloidin. This compound binds tightly to F-actin but in contrast to the cytochalasins it has a stabilizing action on actin filaments. The usefulness of phalloidin as a cytological probe of microfilament organization and function is, however, limited because this toxin is impermeable to most cells. On the other hand, fluorescent derivatives of phalloidin are highly useful for specific visualization of F-actin distribution in fixed cells, and for estimation of F-actin concentration in cells. Thus, until recently, there have been essentially no alternative drugs to the cytochalasins that can serve as useful experimental tools for probing both the mechanisms underlying actin polymerization in vitro, and microfilament organization and function in living cells.

In the light of this situation, our initial discovery that two new toxins from the Gulf of Eilat sponge *Latrunculia magnifica* induce profound changes in cell morphology and; microfilament organization and the results of our subsequent studies of the chemistry, biochemical properties and cell biological effects of the latrunculins have a number of highly significant aspects that can open new fields in microfilament research. See Spector, et al. "Latrunculins: Novel Marine Toxins That Disrupt Microfilament Organization in Cultured Cells," Science, Vol. 219, pp. 493–496 Feb. 4, 1983).

The latrunculins are a novel class of marine natural products isolated from one of the most prominent sponges in the Red Sea, the branching, red colored, *Latrunculia magnifica pk (Keller). Colonies of these sponge grow completely exposed and show no evidence of predation and biodegradation. It has been found that the toxic substances that apparently defend this sponge disrupt microfilament organization may have relevance to the natural history of the sponge and to the chemical defense adaptations of marine organisms. This can be contrasted to the lack of understanding of the physiological functions of cytochalasins as fungal metabolites.*

Structure elucidation of the first two toxins termed Latrunculin A (LAT-A) and Latrunculin B (LAT-B) revealed an architecturally novel class of natural products. See below. The latrunculins are the first marine macrolides known to contain 16- (LAT-A) and 14- (LAT-B) membered rings and they are outstanding in that they appear to be the first natural products to possess the 2-thiazolidinone moiety which is rare in nature. The third major part of the molecule the tetrahydropyran ring (THP) links the macrolide to the thiazolidinone moiety.

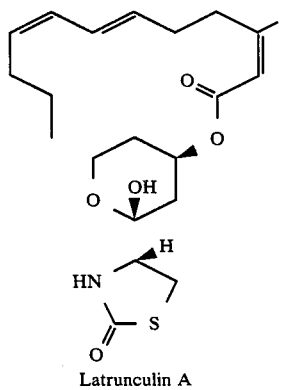

Latrunculin A

-continued

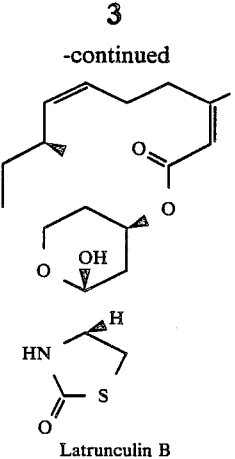
Latrunculin B

Results of studies performed with latrunculins show that they represent a new class of compounds which disrupt microfilament organization in cultured cells. The mode of action of these marine natural products is still unknown. Although some of their effects resemble those of cytochalasins, recently LAT-A was found to affect the polymerization of pure actin in vitro in a manner consistent with the formation of a nonpolymerizable 1:1 molar complex between LAT-A and G-actin. See "Inhibition of Actin Polymerization by Latrunculin A," Martine Coué; Stephen L. Brenner, Ilan Spector, and Edward D. Korn, *FEBS LETTERS.* Vol. 213, No. 2, pp 316–318 (March 1987). These effects are very different from those of filament capping agents such as cytochalasins.

As a result of recent work, the total synthesis of LAT-B has been achieved. See "Total Synthesis of (+)-Latrunculin B," A. B. Smith III, R. Zibuk and N. J. Liverton, J. Amer. Chem. Soc. 108 2451 (1986). Thus, some of the compounds can now be both purified from natural sources and, in the case of LAT-B, synthesized. Pursuant to work performed with homologs of LAT-A and LAT-B it has been found that when alkyl groups are attached to the nitrogen constituent of the 2-thiazolidinone moiety in place of the hydrogen, the compound has become less effective. Thus, artisans have been generally dissuaded from altering this moiety at the nitrogen site.

Studies directed to the activity of latrunculins on cell structure and organization, especially as they relate to other actin toxins such as cytochalasins, show that the effects of the LAT-A and LAT-B ar somewhat varied with respect to normal fibroblast cells and transformed neurosal cells in culture. While both classes of drugs induce changes in morphology and actin organization of the cells within 1 hour of application and inhibit cytokinesis in synchronized cells, the latrunculins exert these short term effects at lower concentrations. Moreover, it has also been demonstrated that while the Latrunculin-B possesses reversibility characteristics, the degree of reversibility in transformed neuronal cells is different from that found in normal fibroblast cells. See Spector, I., Shochet, N. R., Blasberger, D., and Kashman, Y., "Latrunculins: Novel Marine Macroldes that Disrupt Microfilament Organization and Affect Cell Growth, I. Comparison with Cytochalasin D," [submitted for publication] which is incorporated herein by reference. As the characteristics are defined with a high degree of predictability, the ability to employ these novel chemical compounds in a treatment role is enhanced.

Presently, utilization of the latrunculin family of compounds requires a sufficient supply of the compound for the intended purpose. As a research tool, ]Latrunculin-B must be continuously replenished since the effect of Latrunculin-B on cell morphology, actin distribution and cell division is reversible.

There is therefore a real need to provide a latrunculin component which has very high efficacy even at very low dosages. This will enable the researcher to obtain optimum performance with a minimal supply of the drug. Furthermore with respect to the use of latrunculin as a treatment drug, high potency in a small quantity of the drug needed to affect target cells reduces the possibility of unwanted side effects against healthy cells.

Thus, while the discovery of the latrunculin family of compounds has provided exciting research and treatment possibilities, the present invention has quite unexpectedly provided tremendous new capabilities heretofore not anticipated or expected in this technology.

SUMMARY OF THE INVENTION

The present invention is a bio-effecting agent for disruption of cell morphology and inhibition of cell division which includes compounds having the following chemical structures

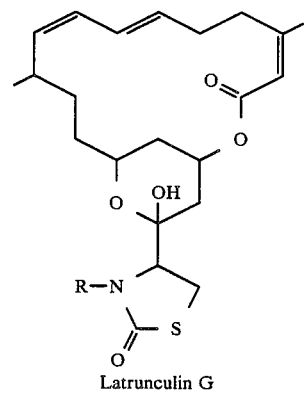
Latrunculin G

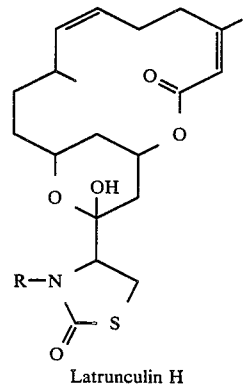
Latrunculin H

Wherein R is —$(CH_2)_n$ZH in which n=1, 2, 3 and 4 and Z is O, S, or NH.

The compounds of the present invention also include those structures which can enhance the ability to direct and/or identify the latrunculin compound in combination with the target cells without interfering with the effectiveness of the compound. These compounds are as follows:

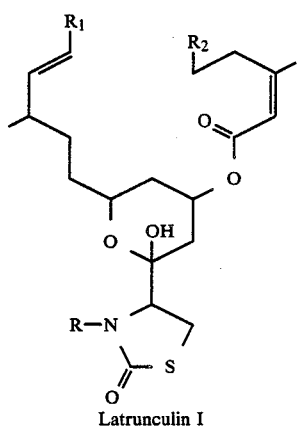

Latrunculin I

Wherein R is —(CH$_2$)$_n$ ZH in which n=1, 2, 3 and 4 and Z is O, S, or NH; R$_1$ and R$_2$ can be —OH, alkyl or acyl.

Agents such as radiolabels, fluorescent labels, antibodies, etc. can then be tagged to the latrunculin compound as desired through the R$_1$ and R$_2$ substituents.

The present invention also contemplates a composition for treatment of cells to change the morphology thereof wherein the above compounds are included in a carrier such as a suitable solvent including, but not limited to, DMSO, ethanol, etc. Since it is presently believed that one preferred method for administration of a latrunculin toxin will be by injection, the solvents are believed to be a preferred form of treatment composition at this time.

The latrunculins of the present invention can be present in an amount of at least about 40 times less than the cytochalasins for the same effect. Thus, even though the naturally found Latrunculins A and B initially reduced the concentration required for effecting cell morphology when compared to that of cytochalasin, the required concentration has been reduced by an even greater degree by use of the present Latrunculins G and H. As research continues and treatment is developed, other advantages will be realized by use of the phenomenally effective Latrunculins G and H.

The unexpectedly high degree of potency provided by the latrunculins of the present invention is considered to be very important with respect to the use of the latrunculins as a treatment drug, since long-term ill-effects can be completely avoided by monitoring and manipulating the administered dosage.

For a better understanding of the present invention, together with other and further objects, reference is made to the following description, and the scope of the invention will be pointed out in the appended claims.

DETAILED DESCRIPTION OF THE INVENTION

The present invention includes the discovery of the highly potent members of the latrunculin family, a new Latrunculin G (LAT-G) and Latrunculin H (LAT-H) as well as Latrunculin I as set forth above. These compounds have astoundingly more drastic effects on the morphology and actin arrangement of living cells than previously discovered Latrunculins A and B, and others.

The structure of the new LAT-A and LAT-B are as follows.

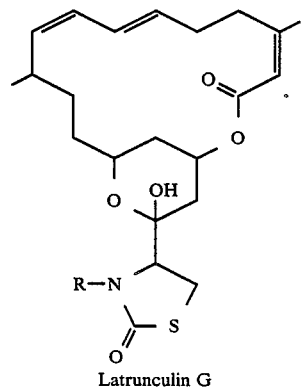

Latrunculin G and

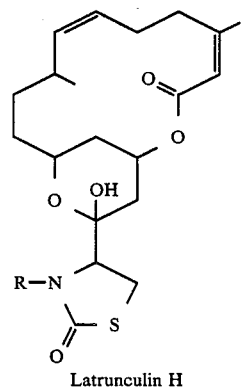

Latrunculin H

Wherein R is —(CH$_2$)$_n$ ZH in which n=1, 2, 3 and 4 and Z is O, S, or NH.

Latrunculin I has been previously described hereinabove.

Procedure For Production Of Latrunculin G

In order to obtain Latrunculin G, 50 mg of LAT-A was warmed for 18 hours at temperatures from about 60° to about 70° C. in a mixture of 40% aqueous formaldehyde (3 ml) and ethanol (2 ml). Twenty-five ml of chloroform was then added, and the organic layer washed three times with water followed by drying over MgSO4 and evaporated. Double chromatography was then performed on a silica gel column which was eluted with ethyl-acetate:heptane at a ratio of 3 to 7. The results yielded 12 mg of pure Latrunculin G.

Latrunculin G was also obtained by purification from the red sponge species *Latrunculia magnifica* by soaking 10 grams of the sponge material in a 4 percent formaldehyde solution. Thereafter the specimen was kept at room temperature for 24 hours and then lyophilized. The lyophilized material was then extracted with heptane and chloroform. Crude extracts were separated on a Sephadex LH-20 column which was eluted with a heptane:chloroform:methanol mixture in a ratio of 2:1:1. The material was then subjected to silica gel with ethyl-acetate:heptane in a ratio of 3 to 7. The result was a purified form of the Latrunculin G compound.

Preparation Of Latrunculin H

Latrunculin H was prepared similar to Latrunculin G by use of LAT-B which was in a quantity of 50 mg which was warmed for about 18 hours at a temperature of from about 60° to about 70° C. in a mixture of 40 percent aqueous formaldehyde (3 ml) and ethanol (2 ml). Chloroform was then added in an amount of about 25 ml and the organic layer resulting therefrom was washed three times with water and then dried over $MgSO_4$. Thereafter the residuum was evaporated and subjected to double chromatography on a silica gel column eluted with ethyl-acetate:heptane in a ratio of 3 to 7. As before a pure Latrunculin H in an amount of about 12 mg was provided.

Latrunculin H was also purified from the red sponge *Latrunculia magnifica* by first of all soaking the LAT-B containing sponge/ in a 4 percent formaldehyde solution and kept at room temperature for about 24 hours. The resulting material was lyophilized and extracted with heptane and chloroform. Crude extracts were separated on a Sephadex LM-20 column which was eluted with heptane:chloroform:methanol mixture in the ratio of 2:1:1 respectively. This was followed by silica gel chromatography using ethyl-acetate and heptane in the 3 to 7 ratio to produce the Latrunculin H.

Comparative Examples

Experiments were then run comparing the activity and efficacy of Latrunculin G and H with the activity of LAT-A and LAT-B. In order to conduct the investigation, transformed mouse neuroblastoma and normal fibroblast cells were used. Immunofluorescence studies were conducted with antibodies which are specific for actin and tubulin.

Cells of transformed mouse neuroblastoma clone N1E-115 were grown in Dulbecco's modified Eagle's medium (DMEM) supplemented with 5 percent fetal calf serum at 37° C. in an atmosphere of 10 percent $CO_2$ in air. Normal mouse fibroblasts (Swiss/3T3) were grown in DMEM supplemented with 10 percent fetal calf serum. Cells were replated into 35-mm plastic tissue culture dishes containing glass cover slips. Differentiated neuroblastoma cells were obtained by adding 2 percent dimethyl sulfoxide (DMSO) to the growth medium.

During the course of the experiments, it was observed that LAT-B at 150 ng/ml, had an effect on the structure of the morphology of the neuroblastoma cells. In particular in about an hour well spread cells lost their smooth contour and assumed a jagged shape and round up in the nuclear region. In morphologically differentiated cells, the neuronal soma rounded up, the cells lost their numerous microspikes, and the shape of the growth cones was markedly altered. With regard to normal fibroblast cells, both LAT-A and LAT-B caused alterations in cellular morphology at a concentration of 350 ng/ml after only about one hour of time.

Further investigation was conducted to determine the effect of the latrunculins on microfilaments by use of direct immunofluorescence microscopy with a purified antibody specific for actin. Treatment with the latrunculins disrupt the organization of actin in the cells. After addition of the LAT-A and the LAT-B at a concentration of 350 ng/ml each, most of the long actin bundles in normal cells are no longer visible, and intense labeling of actin is found in the cytoplasm or in the ruffling membranes. Furthermore, it has been found that once the toxins are removed, the effect of latrunculins on cell morphology and actin distribution is reversible, and within one hour after toxin removal, both the N1E-115 and 3T3 cells regain their normal shape and actin structures.

Similar experiments were conducted using Latrunculins G and H. It was found that after only a very short time, the effect of Latrunculins G and concentration of only 35 ng/ml significantly disrupted normal cell morphology. In the case of transformed cells, a concentration of only 15 ng/ml produced cells with jagged shapes and a nuclear region which was rounded up. With respect to actin organization a concentration of only 35 ng/ml of Latrunculins G and H disrupted long actin bundles.

In general, it has been found through continued experimentation that the potency of the Latrunculin G and H are 10 to 20 times greater than that of Latrunculins A and B. This effect is quite suprising, especially since prior to the discovery of Latrunculins G and H, chemical structures wherein the nitrogen constituent of the 2-thizaolidinone structure modified by addition of straight alkyl substituents proved to be less effective.

Thus, while there have been described what are presently believed to be the preferred embodiments of the present invention, those skilled in the art will realize that changes and modifications may be made thereto without departing from the spirit of the invention as it is intended to include within the scope of the invention all those changes and modifications.

We claim:

1. A compound for disruption of cell morphology and inhibition of cell division selected from the group consisting of

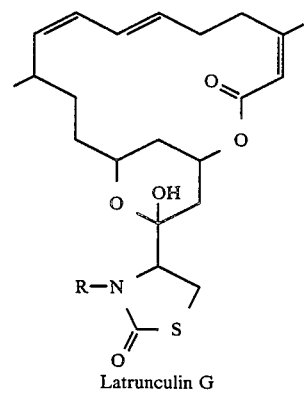

Latrunculin G and

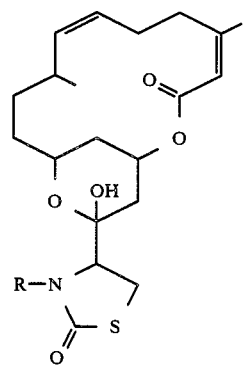

-continued
Latrunculin H wherein R is —CH₂OH, and

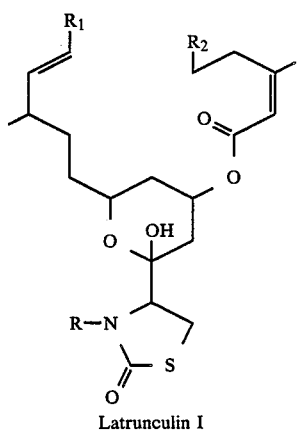

Latrunculin I wherein R is —CH₂OH, and R₁ and R₂ are —OH, alkyl or acyl.

2. A composition for treatment of cells whereby the morphology is irreversibly disrupted comprising a carrier and a compound selected from the group consisting of

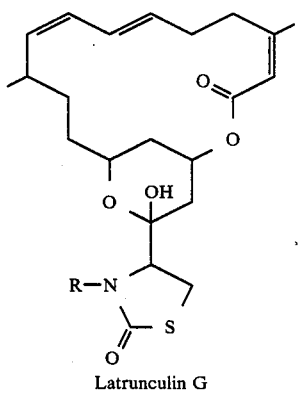

Latrunculin G

-continued
and

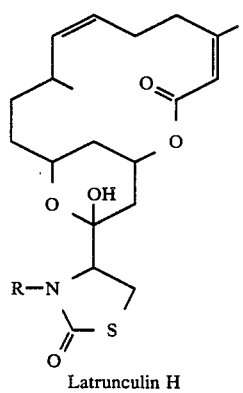

Latrunculin H wherein R is —CH₂OH, and

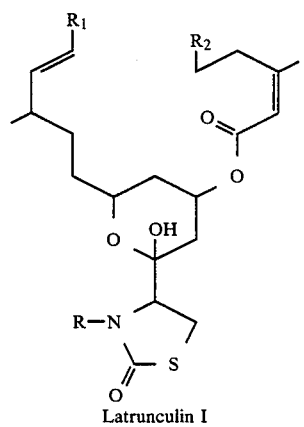

Latrunculin I wherein R is —CH₂OH; and R₁ and R₂ are —OH, alkyl or acyl.

3. A composition of claim 2 wherein said carrier is selected from a liquid carrier.

4. The composition of claim 3 wherein said compound is present in an amount of at least about 7.5 mg/ml.

* * * * *